United States Patent
Burton

(10) Patent No.: US 6,431,171 B1
(45) Date of Patent: Aug. 13, 2002

(54) CONTROLLIING GAS OR DRUG DELIVERY TO PATIENT

(75) Inventor: David Burton, Victoria (AU)

(73) Assignee: Compumedics, LTD, Abbotsford (AU)

( * ) Notice: Subject to any disclaimer, the term of this patent is extended or adjusted under 35 U.S.C. 154(b) by 0 days.

(21) Appl. No.: 09/423,380

(22) PCT Filed: May 7, 1997

(86) PCT No.: PCT/AU97/00278

§ 371 (c)(1),
(2), (4) Date: Nov. 5, 1999

(87) PCT Pub. No.: WO98/50095

PCT Pub. Date: Nov. 12, 1998

(51) Int. Cl.[7] .................. A61M 16/00; A62B 7/00
(52) U.S. Cl. ............... 128/204.18; 128/204.21; 128/204.22; 128/204.23; 128/848; 381/71
(58) Field of Search ............. 128/204.18, 204.21, 128/204.22, 204.23, 848; 381/71

(56) References Cited

U.S. PATENT DOCUMENTS

| | | | |
|---|---|---|---|
| 4,444,201 A | 4/1984 | Itoh | 128/716 |
| 5,047,930 A | 9/1991 | Martens et al. | 364/413.04 |
| 5,134,995 A | 8/1992 | Gruenke et al. | 128/204.23 |
| 5,148,802 A | 9/1992 | Sanders et al. | 128/204.18 |
| 5,188,098 A | 2/1993 | Hoffman et al. | 128/204.23 |
| 5,199,424 A * | 4/1993 | Sullivan et al. | 128/204.18 |
| 5,203,343 A * | 4/1993 | Axe et al. | 128/725 |
| 5,239,995 A | 8/1993 | Estes et al. | 128/204.23 |
| 5,245,995 A * | 9/1993 | Sullivan et al. | 128/204.23 |
| 5,259,373 A | 11/1993 | Gruenke et al. | 128/204.23 |
| 5,313,937 A | 5/1994 | Zdrojkowski | 128/205.23 |
| 5,335,654 A | 8/1994 | Rapoport | 128/204.23 |
| 5,353,788 A * | 10/1994 | Miles | 128/204.23 |
| 5,433,193 A | 7/1995 | Sanders et al. | 128/204.18 |

(List continued on next page.)

FOREIGN PATENT DOCUMENTS

| | | | |
|---|---|---|---|
| AU | A30678/95 | 9/1989 | |
| AU | A33877/93 | 4/1993 | A61M/16/00 |
| AU | A77641/94 | 3/1994 | A61M/16/00 |
| EP | 651971 A1 | 10/1995 | A61B/5/113 |
| WO | WO881010 | 12/1988 | A61F/5/56 |
| WO | WO911357 | 9/1991 | A47C/27/08 |
| WO | WO9211054 | 9/1992 | A61M/16/00 |
| WO | WO9222244 | 12/1992 | A61B/5/08 |
| WO | 9309834 A1 * | 5/1993 | |
| WO | WO9309834 | 5/1993 | A61M/16/00 |
| WO | WO9321982 | 11/1993 | A61M/16/00 |
| WO | WO9416610 | 4/1994 | |
| WO | WO9423780 | 10/1994 | A61M/16/00 |
| WO | WO9532016 | 11/1995 | A61M/16/00 |
| WO | WO9533403 | 12/1995 | A61B/4/0205 |
| WO | WO9640335 | 12/1996 | A61M/15/00 |
| WO | 9640335 A1 * | 12/1996 | |

Primary Examiner—John G. Weiss
Assistant Examiner—Darwin Erezo
(74) Attorney, Agent, or Firm—Fulbright & Jaworski L.L.P.

(57) ABSTRACT

An apparatus is provided for controlling gas delivery to a patient, to maintain effective respiratory function. The apparatus includes sensors for monitoring one or more physiological variables such as breathing airflow sound, EEG, EOG, ENG, and/or patient position. The apparatus includes a determining component for deriving, from the sensed variables, data representing a respiratory event and a component for determining from the data a gas pressure or modulated gas pressure to counteract tissue vibration associated with the respiratory event, thereby tending to cancel the respiratory event. The determining component may include an algorithm adapted to generate a gas pressure signal substantially 180 degrees out of phase relative to the tissue vibration. The apparatus may include a drug delivery module operable to deliver a drug in accordance with the sensed physiological variable and the determining component.

38 Claims, 7 Drawing Sheets

U.S. PATENT DOCUMENTS

| | | | |
|---|---|---|---|
| 5,444,786 A | * 8/1995 | Raviv | 381/71.14 |
| 5,458,137 A | 10/1995 | Axe et al. | 128/204.23 |
| 5,464,012 A | 11/1995 | Falcone | 128/630 |
| 5,485,851 A | 1/1996 | Erickson | 128/716 |
| 5,490,502 A | * 2/1996 | Rapoport et al. | |
| 5,520,192 A | 5/1996 | Kitney et al. | 128/716 |
| 5,522,382 A | 6/1996 | Sullivan et al. | 128/204.23 |
| 5,535,739 A | 7/1996 | Rapoport et al. | 128/204.23 |
| 5,546,933 A | 8/1996 | Rapoport et al. | 128/204.23 |
| 5,549,106 A | 8/1996 | Gruenke et al. | 128/204.23 |
| 5,551,418 A | 9/1996 | Estes et al. | 128/204.23 |
| 5,551,419 A | * 9/1996 | Froehlich et al. | 128/204.23 |
| 5,590,648 A | 1/1997 | Mitchell et al. | 128/630 |
| 5,617,846 A | 4/1997 | Graetz et al. | 128/204.21 |
| 5,645,053 A | 7/1997 | Remmers et al. | 128/204.23 |
| 5,647,846 A | * 7/1997 | Berg et al. | 604/93 |
| 5,704,345 A | 1/1998 | Berthon-Jones | 128/204.23 |
| 5,823,187 A | 10/1998 | Estes et al. | 128/204.23 |
| 5,845,636 A | 12/1998 | Gruenke et al. | 128/204.23 |
| 5,901,704 A | 5/1999 | Estes et al. | 128/204.23 |
| 5,904,141 A | 5/1999 | Estes et al. | 128/204.23 |
| 5,953,713 A | 9/1999 | Behbehoni et al. | 706/16 |
| 5,970,975 A | 10/1999 | Estes et al. | 128/204.23 |
| 6,000,396 A | 12/1999 | Melker et al. | 128/204.21 |
| 6,029,660 A | * 2/2000 | Calluaud et al. | 128/203.12 |
| 6,029,665 A | 2/2000 | Berthon-Jones | 128/204.23 |
| 6,085,747 A | * 7/2000 | Axe et al. | 128/204.23 |
| 6,123,072 A | * 9/2000 | Downs | 381/71.1 |

* cited by examiner

CONTROLLIING GAS OR DRUG DELIVERY TO PATIENT

The present invention relates to apparatus for controlling gas delivery to a patient. The apparatus of the present invention is related to apparatus disclosed in applicant's copending PCT application AU96/00679 filed Oct. 31, 1996 and in AU Patent 632932 entitled "Analysis System for physiological variables", the disclosures of which are incorporated herein by cross reference.

The apparatus of the present invention may provide a diagnostic and/or a therapeutic function. The diagnostic function may include monitoring and/or diagnosis of physiological variables associated with the patient. The therapeutic function may include application of controlled gas delivery to the patient. The diagnostic and therapeutic functions may be performed in a single device having integrated functions or it may be performed via two or more separate devices.

The apparatus of the present invention is particularly useful for investigation, diagnosis and treatment of sleep, respiratory and sleep related respiratory disorders, sleep propensity, fatigue and asthma and will be described herein in that context. Nevertheless it is to be appreciated that it is not thereby limited to such applications.

The apparatus of the present invention has been developed for, but is not limited to monitoring, analysing, storing, controlling and networking physiological variables. The aforementioned "controlling of physiological variables" includes controlling the gas delivery to a patient. This gas can be but is not limited to air as used in a CPAP (Continuous Positive Air Pressure) application, or one of the many variations of positive air pressure delivery to a patient known in the art.

Due to the complex and varying states of sleep and the broad range of sleep disorders that can be diagnosed, many different physiological variables and events can be simultaneously monitored, analysed and stored by the present apparatus. The monitored physiological variables and events can include one or more channels of each of the following signal types:

| | |
|---|---|
| Breathing and snoring sounds | |
| CPAP mask sound | (monitoring for patients breathing sounds within CPAP mask). These sounds include snoring, wheezing and other disordered breathing sounds |
| Brain waves/Electroencephalogram | (EEG) |
| Eye Movement/Electro-oculogram | (EOG) |
| Muscle function/Electro-myogram | (submental EMG from muscles under the chin) |
| Muscle function/Electro-myogram | (diaphragm EMG from respiratory effort) |
| Muscle function/Electro-myogram | (other EMG reflecting muscle and nerve activity either by invasive or non-invasive monitoring) |
| Status of patient position | |
| Leg movements | (Left and/or Right legs) |
| Hear beat/Electrocardiogram | (ECG) |
| Oximetry | ($S_aO_2$ - Oxygen saturation) |
| Carbon dioxide monitoring | $CO_2$ |
| Respiratory effort | (Abdominal, thoracic or otherwise) |
| Airflow | (Nasal or oral) |
| Continuous Positive Airflow | |
| Pressure | (monitoring of patients mask pressure during application of CPAP treatment) |
| CPAP mask temperature | (monitoring of CPAP mask air temperature for breathing activity and airflow of patient) |

Status of lights

Graphic processing of video image (allows determination of whether patients eyes are open or closed).

Patient digital video recording and graphic processing techniques for determination of eye lid activity (ie status of patient eyes being opened or closed—relative to fully closed or fully opened eyes status).

Time and date stamping of monitored physiological data, video and sound.

Infrared Video monitoring (for night studies)

Complex sound analysis (accurate full bandwidth or limited bandwidth recording and analysis of breathing sounds. The sound is analysed and compared with criteria or a data base, consisting of reference data for disordered breathing. Microphones may be servo controlled for automatic axis adjustment to allow optimum focus on breathing sounds.)

Physiological events: ie ECG arrhythmia, EEG spike detection, EEG spindles amongst others Local area networked monitoring, analysis and/or storage of a patient's physiological variables Endoscopy Breath by breath analysis-pnuemotachograph 3D imaging Virtual patient monitoring Infrared eye detection for fatigue and sleep monitoring EEG delta and alpha-wave detection Eye position and movements by way of Infrared Eye Detection Delta Wave detections and related sleep/fatigue/impairment detection Mattress Device: monitoring of patient sleep state and respiratory parameters by using a mattress sensor device. The matress device can be used to monitor a patient's electro-oculogram, sleep state; arousals, position, electrocardiogram. There are presently two types commercially available mattress devices; Static Charge-sensitive Bed (SCSB) and polyvinylidene fluoride (PVDF—piezoelectric plastic).

When monitoring sleep states, sleep propensity, respiratory disorders, vigilance state or fatigue of a subject, one or more physiological variables as listed above may be continuously monitored and/or analysed and/or stored.

The present invention allows one or more channels of patient variables and/or events to be monitored, processed and recorded, while at the same time allowing precise data interconnection with a remote site. This remote site can view, process or record the real-time patient data. The communication link can take the form of a range of transmission media, including but not limited to wireless interconnection such as spread spectrum transmission wireless LAN.

The prior art provides devices for the purpose a patient's breathing but these devices are unable to apply principles of acoustic cancellation as proposed by the present invention. While the applicant appreciates the prior systems can monitor patient breathing sound and in particular snoring, these earlier devices were not developed to modulate gas delivery to a patient in a way which can acoustically cancel vibration in the patient's upper palate.

According to the present invention there is provided apparatus for controlling gas delivery to a patient's, said delivery being indented to maintain effective respiratory function, said apparatus including:

a monitoring component adapted to monitor at least one physiological variable o f a patient during an application of a positive gas pressure to an airway of the patient, to provide monitoring information representing the at least one physiological variable; and a processing component including a deriving component in communication with the monitoring component to receive the monitoring information and, based on the monitoring information, to derive data representing a respiratory event characterized by vibration of body tissue along the airway;

said processing component further including a determining component coupled to receive said data and adapted to generate a control signal based on said data, said control signal including a modulated component that is substantially 180 degrees out of phase relative to said data and being applicable to control a gas delivery device to modulate said positive gas pressure in accordance with the modulated component of the control signal to counteract said vibration of body tissue, thereby tending to cancel the respiratory event.

The monitoring means may include means such as a plurality of sensors and/or transducers for acquiring and monitoring variables representing physiological states associated with the patient. The physiological variables can include respiratory effort, breathing airflow, oximetry and/or sound. To this end the monitoring means includes an air pressure wave or sound/acoustic vibration transducer to monitor breathing sound and/or air pressure waves associated with the patient's respiratory function. The air or sound pressure wave transducer may include a sound microphone, air pressure sensor, air flow sensor or similar device. The air/sound pressure wave transducer may be located near the patient such as being incorporated in the nasal or nasal and oral mask used to deliver gas to the patient, or at any other location suitable for monitoring patient airflow and/or sound. Alternatively or additionally the apparatus may include other respiratory parameters input for the purpose of monitoring and detection of respiratory effort and/or respiratory disorders.

The or each sensor and/or transducer may generate an analog signal representative of variables being monitored. The monitoring means may include means for amplifying and/or performing analog processing on the analog signal. The latter may perform filtering and/or other wave shaping functions. The processed signal may be fed to an analog to digital converter to convert the or each analog signal to a corresponding digital signal. The or each digital signal may be fed to a digital processor such a microprocessor or microcomputer. The digital processor may include software for deriving from the or each digital signal data representing the patients respiratory state. The software may include means such as an algorithm for determining from the data a gas pressure value which substantially prevents a deterioration of the respiratory state. The algorithm may be adapted to generate a gas pressure signal which is substantially 180° out of phase relative to the phase of the patient breathing air flow and/or sound together with an option of a further gas pressure signal which changes relatively slowly when compared to the out of phase signal. The latter may be used to control delivery of gas to the patient to cancel out or substantially compensate the effects of a breathing disorder. In the event that the breathing disorder is not substantially corrected the software may be adapted to activate delivery of a drug such as ventilum. This may circumvent what may otherwise be a fatal or severe asthma attack. The software may additionally be adapted to determine quantity requirements of the drug. The latter may be based on the patient's history and the extent to which the disorder fails to respond to gas pressure treatment.

A preferred embodiment of the present invention will now be described with reference to the accompanying drawings wherein.

Figure 1:
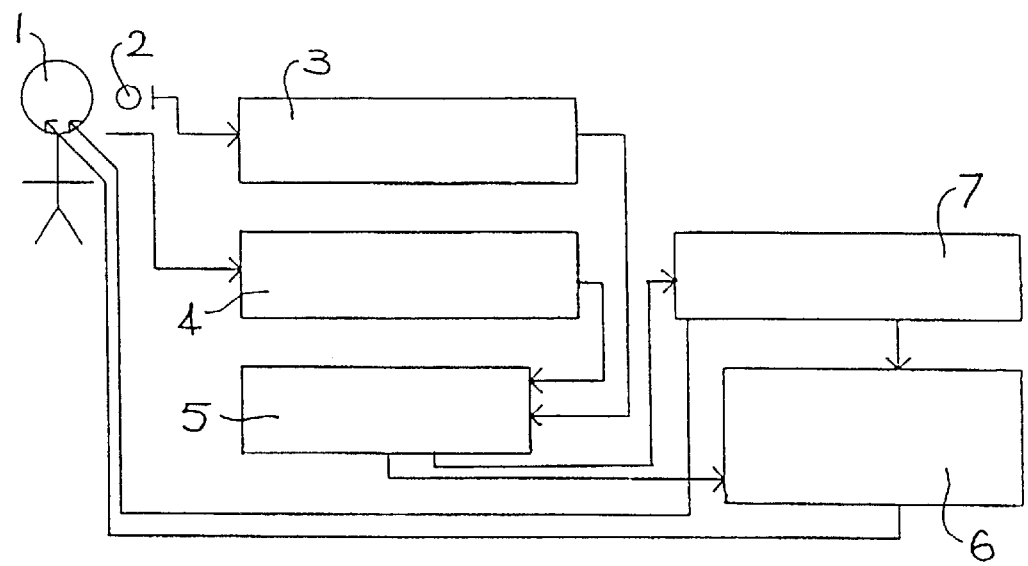
FIG. 1 shows a block diagram of one form of gas delivery apparatus according to the present invention.

Referring to FIG. 1 of the drawings, microphone 2 picks up sound from patient 1 and converts this to an electrical signal. The electrical signal from microphone 2 is analog in nature and is passed to signal amplifying and processing module 3.

Amplifying and processing module 3 amplifies the analog signal and performs filtering and/or wave shaping as required. The analog signal then passes to module 5. Module 5 also receives data from one or more sensors and/or transducers adapted to monitor a range of physiological variables associated with patient 1 such as respiratory effort, respiratory airflow, patient oxygen saturation, brain waves (EEG), heart beat (ECG), eye movement (EOG) muscle function (EMG), patient position and the like. The latter are represented by module 4 which provides analog signals representing the monitored physiological variables to module 5.

Module 5 includes one or more analog to digital convertors and a digital central processing unit (CPU) such as a microprocessor or microcontroller. The CPU is loaded with software including one or more processing algorithms for generating, inter alia, a gas control signal. The gas control signal may be adapted to produce a constant or varying gas pressure and/or air flow as required to compensate a prevailing respiratory disorder.

The gas control signal is fed to pressure transducer 6 to produce a gas pressure which is of a similar frequency but is substantially 180° out of phase relative to the phase of the respiratory signal picked up by microphone 2. The antiphase gas pressure produced by pressure transducer 6 is fed to the patient 1 via a conduit such as a plastics tube and may be applied via the nasal or nasal and oral mask to substantially cancell or compensate the effect of the prevailing breathing disorder. Pressure transducer 6 may include a pressure valve for controlling gas pressure or an acoustic transducer such as a loudspeaker driver.

The apparatus optionally includes a drug delivery module 7 for delivering a drug such as ventilum to patient 1 directly or via the gas feed associated with pressure transducer 6.

Drug delivery module 7 receives its control signal from the digital processing unit of module 5. The signal to initiate drug delivery may be based on a consideration of a large number of patient variables available to module 5 via module 4.

Referring to FIGS. 1A to 1F, FIG. 1A shows typical sound pressure waveforms associated with a snoring patient. The sound pressure waveforms impinge upon microphone 2. Successive bursts of waveforms are shown separated by a time "t". Where the time "t" is greater than about 10 seconds this may be interpreted by module 5 of the apparatus as an apnea episode.

Figure 1A:
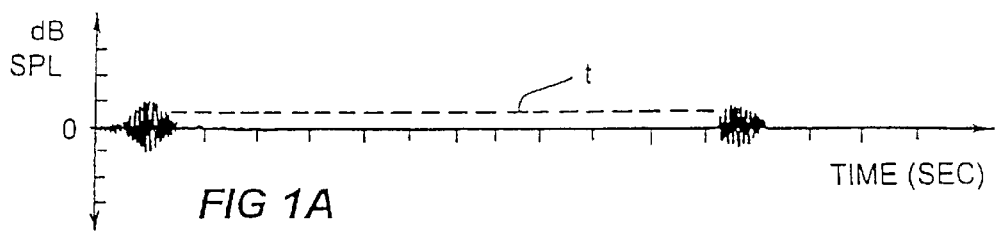
FIGS. 1A to 1F show waveforms associated with the apparatus of FIG. 1.
Figure 1B:
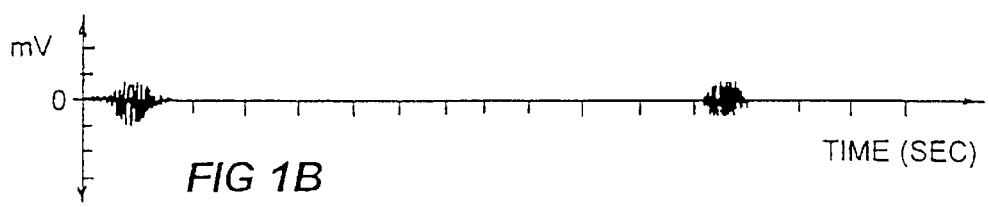

FIG. 1B shows the analog electrical signal at the output of microphone 2 which is inputted to amplifying and processing module 3 in FIG. 1.

Figure 1C:
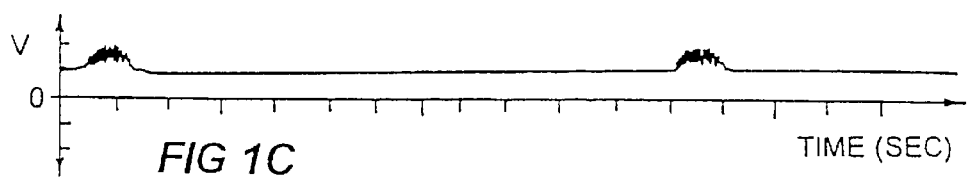

FIG. 1C shows the (analog) gas control signal outputted by module 5 and inputted to module 6 in FIG. 1.

Figure 1D:
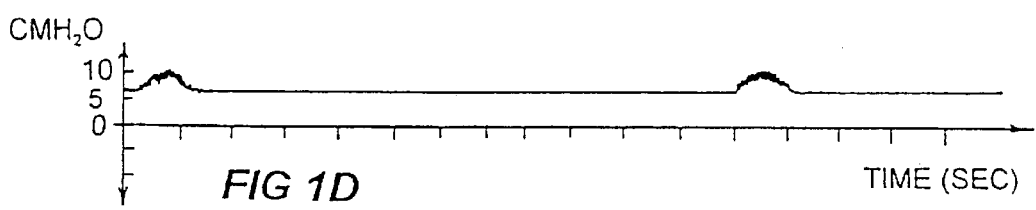

FIG. 1D shows the actual airflow/pressure associated with the gas (air) delivered via a conduit from module 6 to patient 1.

Figure 1E:
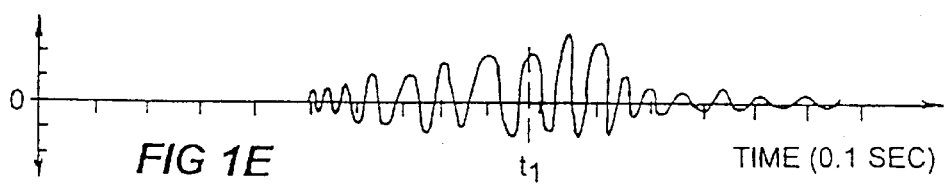

FIG. 1E shows the sound pressure waveform of FIG. 1A in which the (horizontal) time axis has been expanded by a factor of 10.

Figure 1F:
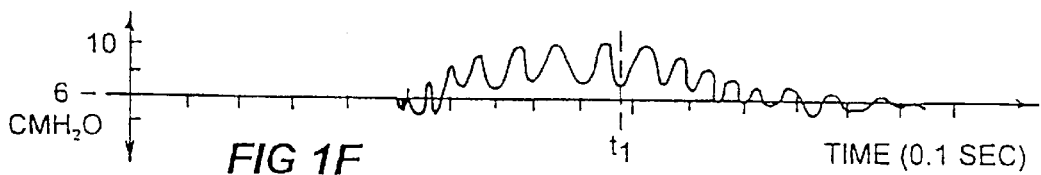

FIG. 1F shows the actual airflow/pressure of FIG. 1D in which the (horizontal) time axis has been expanded by a factor of 10.

A comparison of the waveforms FIGS. 1E and 1F shows that at time $t_1$ a peak in the waveform of FIG. 1E is accompanied by a trough in the waveform of FIG. 1F, illustrating the phase reversal which gives rise to acoustical cancellation and compensates the effects of a prevailing breathing disorder.

Figure 2:
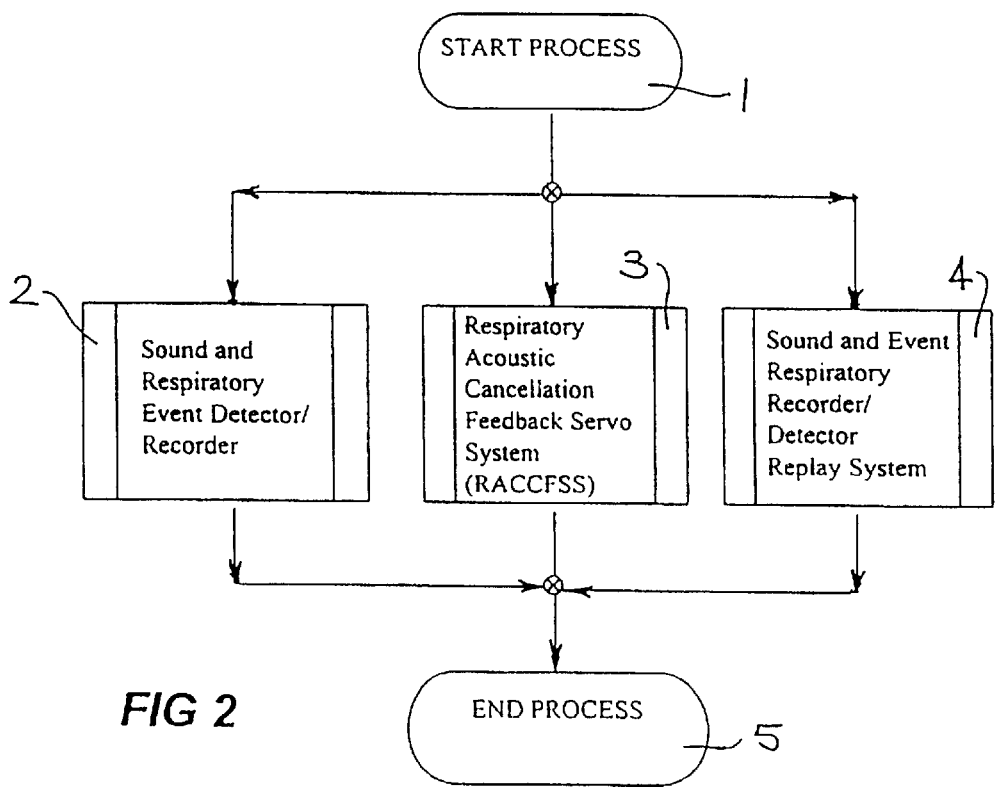
FIG. 2 shows an overview of system software which may be used in conjunction with the apparatus shown in FIG. 1.

Referring to FIG. 2 of the drawings, a combination of the following processes can be operated in real-time either individually or concurrently at any time.

(a) Sound and respiratory event detector/recorder.

(b) Sound and respiratory event detector/recorder replay system.

(c) Acoustic feedback servo system.

The following is a description of each mode of operation with reference to a typical application, being snore detection.

BLOCK 1

Block 1 represents the start of the system processes. Start can be initiated by selecting start recording from system control. Alternatively start process can be initiated by configuring the system to start at a predefined time or the device can be started automatically on power up of the apparatus.

BLOCK 2

Sound and Respiratory Event Detector/Recorder

Block 2 represents the system's event detection and recording function mode. The apparatus may be used with minimal memory requirements, in which case the processing capabilities of the system to detect and record the occurrence and frequency of events such as snoring, allows a basic detection device.

For example, the apparatus may be used to monitor patient's breathing sounds and record the events for purpose of a snore index which may allow a physician to determine the extent to which a patient is snoring. The apparatus may detect the frequency and severity (by way of amplitude or sound level measurement) of snoring by a patient. This is the simplest operation mode of the apparatus as memory requirements are minimal. The original sound does not need to be recorded and the apparatus is set up to detect snore events only and count them per unit time such as each hour, for example. By providing to a medical practitioner an indication of how many snores per hour are detected, and the sound level of these snores, the patient can be recommended for further more advanced diagnosis and/or treatment if required.

Alternatively the apparatus can be operated in a mode to store raw data from the input microphone and/or other input sensor(s). This mode of operation can be operated in conjunction with the simpler above mentioned detection mode to allow the medical practitioner to detect a patient's breathing disorders such as snoring, while at the same time, provide a means of allowing the practitioner to review the patient raw data and validate the detection accuracy of the apparatus.

The former method of detection without the raw data recording function has the advantage of providing a lower cost device in that the memory requirements are less where the device only has to record the occurrence of an event and the time of this occurrence, as opposed to the recording of all the original raw data from the input signal(s).

BLOCK 3

Respiratory Acoustic Cancellation Feedback Servo System (RACFSS)

RACFSS represents a mode of operation which allows the monitoring of a patient's breathing sounds such as snoring, while at the same time generating a control signal to provide a modulated gas delivery to a subject. The phase and airflow of the modulated gas delivery to the patient is related to the monitored sound signal from the patient. This is because snoring, due to the vibration of the patient's upper palate, can be cancelled out or nulled out by way of an acoustic or pressure waveform of opposite polarity to the original sound source. In the example of snoring, vibration of the upper palate is counteracted by a pressure modulating the patient's palate in opposite polarity to the sound pressure waveforms originating the patient's snoring. This "opposite polarity" pressure or acoustic cancellation can be applied to the patient by way of a nasal mask or a full nasal and oral mask. The delivery of the modulated gas to the patient is preferably such that the patient's breathing is stabilised with a minimum amount of gas.

The signal monitored from the patient can be sound, airflow, respiratory effort or other means of detecting the patient breathing.

This control of gas delivery is able to "track" the sound monitored from a patient in such a manner that sound pressure waves produced from the physiological effects of snoring (for example) can be cancelled out by applying a base pressure with a modulated pressure signal of opposite acoustic phase to the originating patient's snore sound.

While the prior art includes Continuous Positive Air Pressure (CPAP) devices (Sullivan), Variable Positive Air Pressure devices (VPAP), Demand Positive Pressure devices, Autoset (designed by ResMed to automatically adjust CPAP pressure), the apparatus of the present invention is able to apply a modulated pressure waveform with a fast dynamic range and frequency together with a base line pressure, in order to provide acoustic cancellation of patient physiological sounds such as snoring. This type of gas delivery device requires application of unique pressure drivers such as a diaphragm in order to apply the modulation at a frequency high enough to acoustically cancel out a patients snoring with minimal modulated air pressure/flow and minimal base level pressure.

The process of Block 3 can operate individually or in combination with the processes of block 2 or block 4. When Block 3 is operated as an individual process the system is used in a mode of therapeutic control whereupon a subject can be treated for disorders such as apnea, snoring, hypopnea, amongst others.

BLOCK 4
Sound and Respiratory Event Detector/Recorder Replay System

Block 4 represents the systems capability to provide a means to review:

a) monitored raw data input from the microphone;

b) review events detected by the apparatus in order to validate the precision and accuracy of event detection capabilities of the apparatus. This function is helpful to provide to a user of the apparatus a level of validation supporting any diagnostic decision that evolves from the use of the apparatus;

c) Selective or random sample event storage. This mode of operation allows the apparatus to store one or more selective or random samples of detected events. While only a limited set of raw data samples are stored, all events may be detected, counted and summarised in terms of events per unit time eg. per hour. This technique may reduce storage requirements significantly while still providing a means for validating a recorded event by recording one or more typical detected events. An example where this function would be useful is where a patient is monitored for snoring but where false detections through excessive background noise could be indicated by allowing the user to review some sample recorded events, which may include excessive background noise, and indicate that the system results should be observed with caution.

Figure 3:
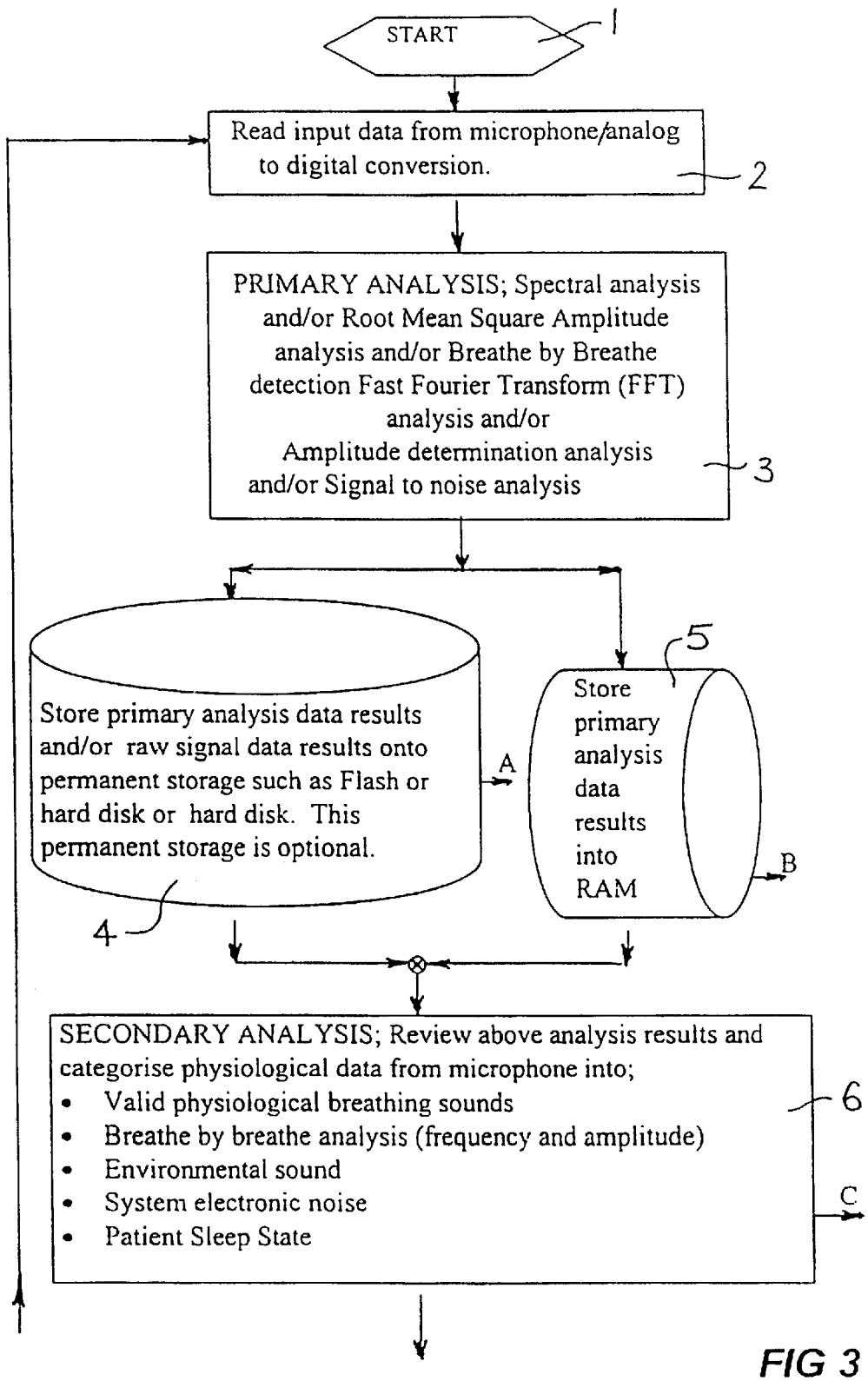
FIGS. 3, 3A and 3B show a flow diagram of the sound and respiratory event detector/recorder.
Figure 3A:
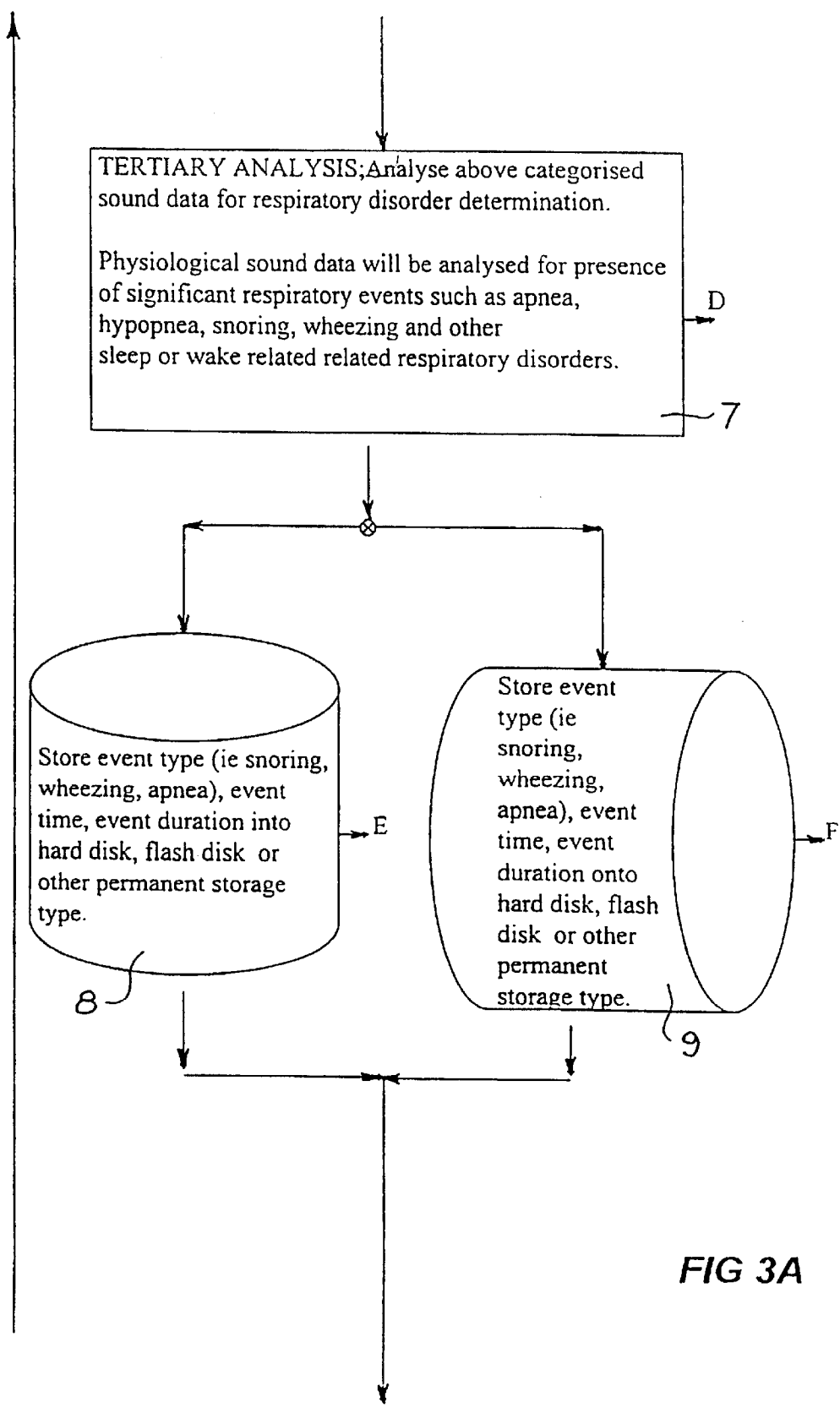
Figure 3B:
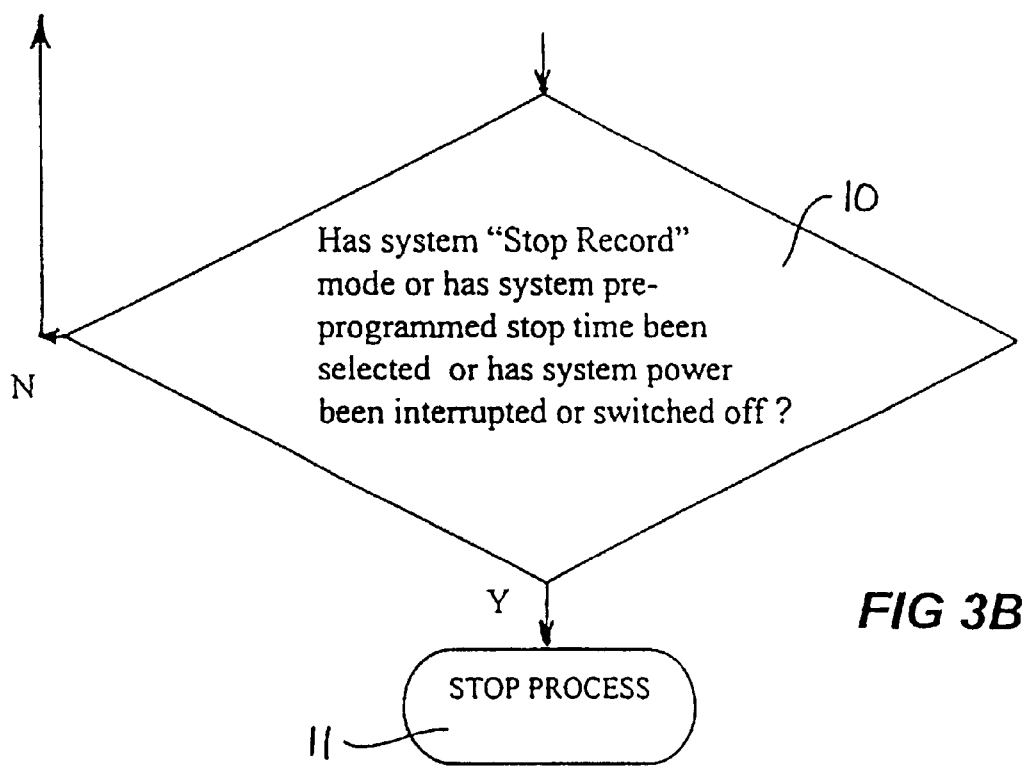
Figure 4:
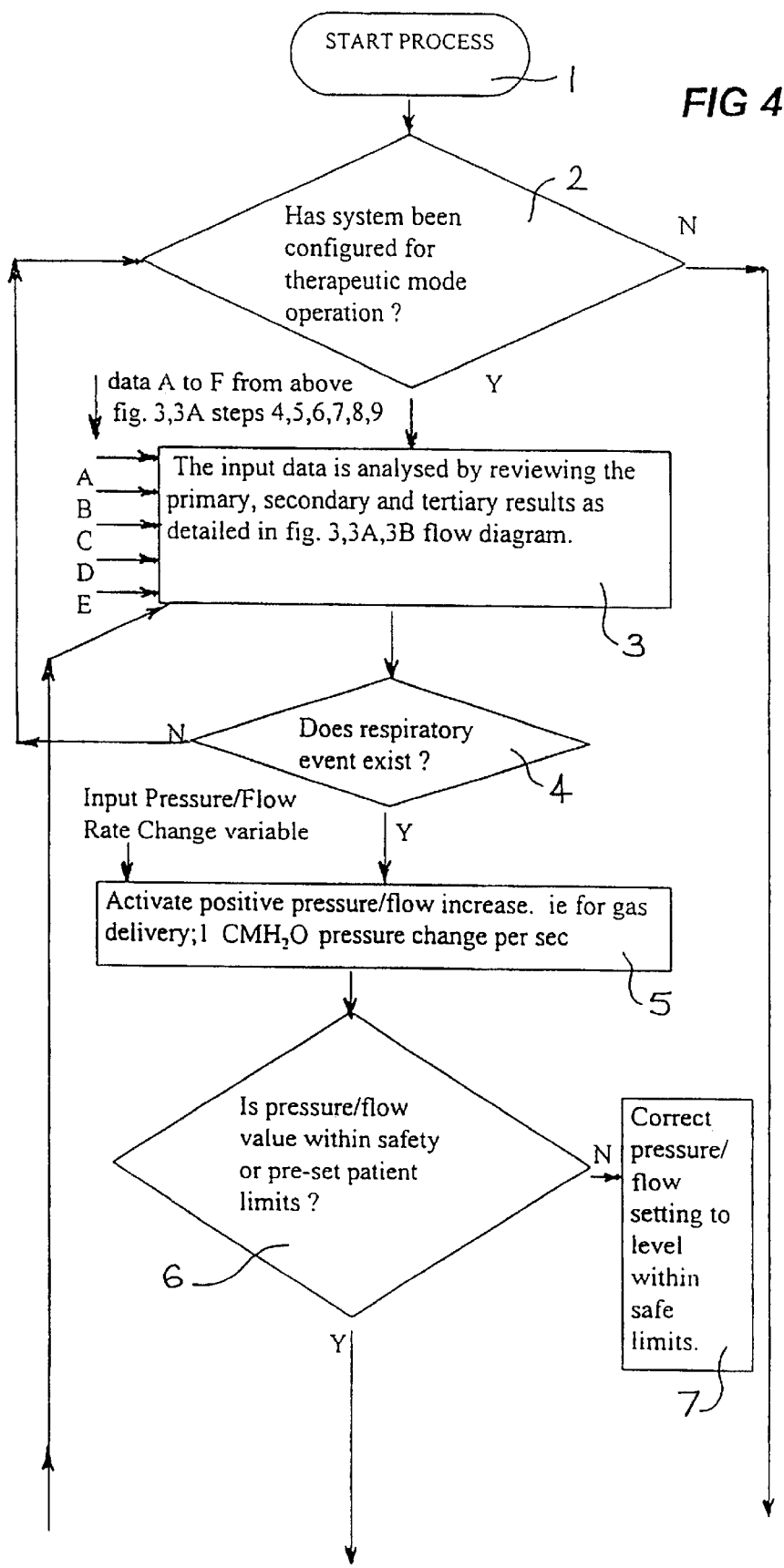
FIGS. 4 and 4A show a flow diagram of the respiratory acoustic cancellation feedback servo system.
Figure 4A:
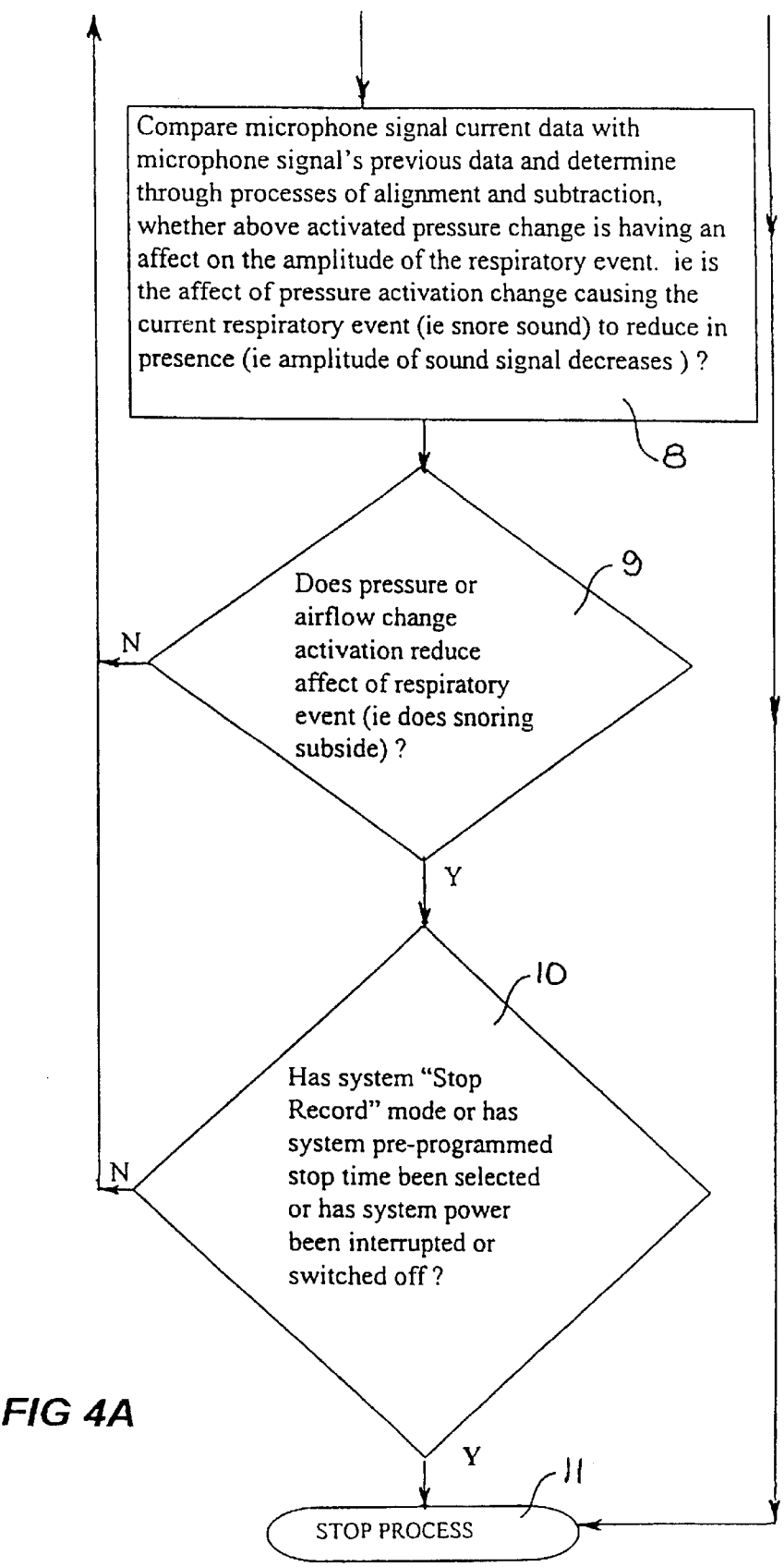

A flow diagram associated with operation of Block 2 (sound and respiratory event detector/recorder) in FIG. 2 is shown in FIGS. 3, 3A and 3B. With reference to FIGS. 3, 3A and 3B the following is a description of the steps associated with Block 2.

STEP 1

Step 1 represents the system start which could be operated by selecting power on, the pre-programming of a particular start-time, by applying power to the apparatus or alternatively by remote start command.

STEP 2

Step 2 represents converting of data from the input source to a digital format so that this can be further processed in digital mode by the central processing unit of the apparatus. This input data can be, but is not limited to the input from a microphone. Alternatively or additionally the input data can be from other means of detecting patient breathing which could be for example from; an airflow sensor such as a thermistor breathing sensor, thermo-coupler breathing sensor, respiratory effort sensors, sounds recorded from a patient breathing mask (nasal or nasal and oral), a vibration sensor device attached to the patient or other means of monitoring the patient's breathing sounds or physiology.

STEP 3

Step 3 represents primary processing capabilities of the apparatus including the following:
Breathe by Breathe Detection Breathe by breathe analysis allows the "zero crossing" of each breathing cycle to be detected in order to separately classify each patient's breathing cycle. Classifying each breathing cycle allows secondary and tertiary analysis to compare a current patient breathing cycle with a previous breathing cycles in order to determine any change in characteristics of the patient breathing. This is a necessary function when determining whether the application of RACFSS is having the desired affect in relation to stabilising the patient's breathing, ie. is the application of increased and/or modulated air pressure or airflow by way of nasal breathing mask removing the symptoms of snoring, or is the application of ventilum by way of face mask removing the symptoms of asthma (ie is wheezing subsiding). Both these examples are direct applications of RACFSS.

Spectral Analysis (SA)

SA provides a breakdown of the frequency spectrum in terms of amplitude and frequency bands. This type of analysis can also incorporate amplitude or half-period-amplitude analysis. The sample period for spectral analysis can be varied within the processing stages to determine both recognition of instantaneous breathing sound changes and longer term breathing sound changes. The parameters by which the SA processing variables are configured are determined by the user of the apparatus or preset from clinical studies.

Fast Fourier Transform (FFT)

FFT is a conventional form of analysis and is provided for the purpose of determining the power monitored at various frequencies. The sample period for the FFT can be varied within the processing stages to determine both recognition of instantaneous breathing sound changes and longer term breathing sound changes. The parameters by which the FFT processing variables are configured are determined by the user or the apparatus or preset from clinical studies.

Amplitude Determination Analysis

Amplitude of the input microphone signal can be determined for the following conditions;

each period amplitude each ½ period amplitude average amplitude over various time intervals (ie ½ second, 1 second, 5 seconds, 10 seconds, 20 seconds, 30 seconds, 1 minute, 5 minutes). running average amplitude- ie average level recalculated after each new ½ period or period of monitored signal where the interval for average amplitude can be ½ second, 1 second, 5 seconds, 10 seconds, 20 seconds, 30 seconds, 1 minute, 5 minutes or other durations.

The period over which the signal average is determined can be configured by the user of the apparatus or preset from clinical studies.

Signal to Noise Analysis

Signal to noise analysis can determine normal system noise by shorting out input stage electronics and removing external sound, in order to calibrate the system for external noise against system electronic noise. Advanced signal to noise analysis can also distinguish, in part, patient breathing sounds against unwanted room noise. The determination of background noise can allow accurate threshold calculation in order to precisely set a point at which microphone signal should be ignored.

STEP 4

Step 4 represents an optional capability of the apparatus to store monitored patient data together with primary analysis data onto permanent or semi-permanent devices such as hard disk or removable flash disk devices. This function is indicated as optional because the apparatus can be configured with no or minimal permanent or semi-permanent storage capabilities in order to reduce the manufacturing cost of the apparatus.

This type of storage is necessary to ensure that raw data from the monitored patient input can be reviewed either remotely or locally during the systems operation or at a later time. The reviewing of the data can be required by the physician or user of the apparatus. A review of this raw data allows a validation of the type of information monitored by the apparatus and also allows the apparatus to indicate to the user where and what events were detected. Thus the user of the apparatus can validate the detection algorithms and processing capability of the apparatus, which is an important factor in the use of the apparatus for providing reliable patient diagnosis.

If, for example, the apparatus is used in noisy environments the number of false event detections may increase and render operation of the apparatus unacceptable. This may be determined by viewing the recorded data and noting whether any events were undetected or falsely detected by utilising an experienced person's capability in scrutinising system performance.

STEP 5

Step 5 represents the system's RAM which can be used to store various processing requirements of the apparatus, together with minimal data storage requirements such as the detection of events, the frequency of detection of events (ie events per hour), random or selective storage of events, patient identification, amongst other storage requirements.

STEP 6

Step 6 represents secondary processing capabilities of the apparatus. This includes an ability to review the output of the primary analysis determined in step 3 above and stored in step 4 and/or 5. The various primary output data needs to be correlated with each type of secondary analysis in order to provide a more accurate means of identifying valid secondary physiological events. For example the recognition of longer term physiological breathing patterns as distinct from shorter term and irregular environmental noise provides a basis of more accurate detection than detections involving less processing and having less discriminatory detection capabilities.

Valid Physiological Breathing Sounds

Valid "physiological breathing sounds" refers to sound recorded from the patient as opposed to background electronic system noise and background room noise. Signal to Noise analysis (step 3) deals with calibration of system noise while the calibration of room noise against physiological noise is more complex due to the vast variety of possible room noise. "Physiological breathing sounds" refers to normal breathing sounds and various disordered breathing sounds such as snoring, wheezing, coughing, amongst others. Physiological breathing sounds may be determined by comparing actual data (refer to A, B, C, F in FIG. 3.) to prestored data that characterise various breathing and sleep disorders. The prestored data can be determined by comprehensive clinical trials.

Real-Time Breathe by Breathe Analysis (Frequency and Amplitude)

Breathe by breathe frequency analysis can be analysis classification of each breathing cycle in terms of amplitude, spectral and/or fast fourier transform data. These frequency and amplitude characteristics as determined for each breathing cycle (where each breathing cycle is detected in step 6 above) are then collated in terms of frequency and amplitude characterisation for each and every breathing cycle. By characterising each breathing cycle in this manner it is possible to provide a level of background noise discrimination (environmental and electronic system noise). This noise discrimination is possible as breathing noises can be related to the peak and trough points of the breathing cycle, for example. Background noise will not be associated with the breathing cycle as will physiological breathing noises. This is an example of how noise discrimination can be implemented within step 6.

Environmental Sound

Environmental noise is the total sound recorded minus the electronic signal noise and the physiological breathing sounds.

A "patient's sleep state" can be determined by the apparatus by simple means such as arousal detection. These arousal detections can be by way of monitoring additional channels such as movements from a special sensitive mattress. The mattress may be a piezo ceramic or capacitive discharge type. In both these aforementioned mattress types the apparatus is able to monitor the frequency, amplitude and regularity of patient body movements as an indicator as to whether or not the patient is likely to be asleep.

STEP 7

Step 7 represents tertiary processing capabilities of the apparatus. This includes a final analysis by referencing the information from step 6 (which determines valid physiological events as opposed to background and system noise-secondary analysis) and categorises the physiological event data into categories as recognised by medical physicians in the determination of a patients respiratory disorder or sleep disorder diagnosis.

This categorisation can include recognition of an apnea event. The latter is typically recognised by a lapse in breathing during a "patient's sleep state" for a period greater than 10 seconds. In the context of the present invention this could be recognised by detection of snoring sounds punctuated by relative breathing silence for 10 seconds or greater. This type of analysis and categorisation can provide a means of presenting a snoring index or number of snores per hour. The number of snores per hour is recognised by the medical user of the apparatus as an indicator that the patient is suffering from Obstructive Sleep Apnea for example.

By comparing the patient's current and context (ie the context of the current sound amplitude and frequency with respect to previous sound characteristics) sound amplitude and frequency characteristics with the reference data base characterising various breathing disorders, accurate classification of patient's respiratory disorder is possible. Common, but often under-diagnosed disorders such as asthma can be detected effectively with a simple representation of the present invention by allowing the sound analysis to detect wheezing as could be characteristic of asthma or asthma onset. Wheezing, for example, can be characterised by a pre-stored set of parameters which represent typical characteristics expected when a wheezing signal is detected. These typical wheezing parameters are determined by clinical studies. This technique of comparing a currently monitored patient signal characteristics with the signal characteristics from a range of typical parameters from a sample of respiratory disorders, assists the apparatus of the present invention to provide quick and accurate detection of a number of respiratory disorders with minimal channels required for monitoring (ie in the most common implementation of RACFSS, a simple microphone channel).

Step 7 also has the function of comparing each patient's breathing cycle with a data base of patient breathing characteristics. This data-base of breathing characteristics which may be derived from prior clinical studies, allows matching of frequency and amplitude characteristics of various breathing disorders. In this way a comparison of the current patient's frequency and amplitude characteristics with a known data base of characteristics and associated disorders may assist in accurate diagnosis of the patient's breathing disorders. For example, if the patient is wheezing, the frequency and amplitude characteristics of this sound analysis is likely to match with the reference data base for a diagnostic classification of wheezing, which together with other patient states may lead to the diagnosis of asthma. This diagnosis may lead to the delivery of ventilum.

The output state or event in this case could be high level wheezing. In this example of wheezing RACFSS could be replaced with a ventilum delivery device as the feedback element. The application of ventilum to the patient as the feedback element to cancel out the acoustic symptom of wheezing manifests itself as a precise and accurate method of delivering the absolute minimum but highly responsive treatment of wheezing-related asthma.

The ventilum track algorithm could, for example (in a therapeutic mode of the apparatus) increase or decrease ventilum delivery to the patient until the wheezing state ceases. The optimum value of ventilum delivery could then be stored into a diagnostic ventilum set look-up-table (for later diagnostic reference by the supervising medical practitioner). Various values for ventilum delivery could therefore be determined in this way having regard to each patient state or breathing event.

STEP 8

Step 8 represents a capability of apparatus to store the monitored event type (ie snoring, wheezing, apnea), event time, event duration into hard disk, flash disk or other permanent or semi-permanent storage type.

This function may be optional because as noted above the apparatus can be configured with no or minimal permanent or semi-permanent storage capabilities in order to reduce the manufacturing cost of the apparatus. A review of this raw data allows a validation of the type of information monitored by the apparatus and also allows the apparatus to indicate to the user where and what events were detected. Thus the user of the system can validate the detection algorithms and processing capability of the apparatus, which is an important factor in the use of the apparatus for providing reliable patient diagnosis.

STEP 9

Step 9 represents the system's RAM or other permanent storage facility which can be used to store various processing requirements of the apparatus, together with minimal data storage requirements such temporary storage of tertiary analysis results. Temporary storage can be suitable for the purpose of providing to the user of the apparatus, a means of having a summary of the patient diagnosis. This diagnosis in the simplest form could be, for example, a snoring index (eg. snores per hour).

STEP 10

Step 10 provides "Stop Record" mode. This is achieved by detecting whether the system has a valid pre-programmed stop time, whether the system has been selected for off or whether the system power has been switched off.

STEP 11

Step 11 ends the process and follows step 10 system off selection.

A flow diagram associated with operation of Block 3 (respiratory acoustic cancellation feedback servo system—RACFSS) in FIG. 2 is shown in FIGS. 4 and 4A. With reference to FIGS. 4 and 4A, the following is a description of the steps associated with Block 3.

STEP 1

Step 1 represents the system start which could be operated by selecting power on, the pre-programming of a particular start-time, by applying power to the apparatus or alternatively by remote start command.

STEP 2

Step 1 represents the function of the device which detects the system user's selection of therapeutic mode. The selection of therapeutic mode is optional and allows the system to provide control for a gas delivery device, while at the same time providing detection and monitoring of respiratory disorders. The therapeutic function may not be required where the apparatus is to be used as an indicator of snoring or apnea but would be required where the apparatus is to be used for the purpose of monitoring sound while at the same time providing gas delivery control utilising the acoustic cancellation capabilities of the apparatus.

STEP 3

Step 3 analyses input data including microphone input data. The input data is analysed by reviewing the primary, secondary and tertiary results as detailed in the flow diagram of FIG. 3.

It is necessary to determine whether an event such as snoring has commenced in order to prepare the apparatus to operate in RACFSS mode.

STEP 4

Step 4 decides whether a respiratory event or the start of a respiratory event is detected. The apparatus will prepare itself to track the signal amplitude detected from a respiratory event in order to be able to produce a control signal for the purpose of physiological event cancellation by way of gas delivery.

STEP 5

Step 5 produces the control signal for the purpose of providing an appropriate base level pressure and modulated pressure.

This control signal contains both a base level or low frequency pressure or airflow control and a higher frequency modulated pressure or airflow control. The apparatus produces the control signal for controlling an external device. Alternatively the apparatus could be integrated into a gas delivery device which provides the capability to regulate the pressure or airflow to the patient's face mask (i.e. nasal or full mask).

This pressure control can be similar in frequency and opposite in phase to the original acoustic waves as detected by the microphone. The apparatus should have sufficient processing capability to produce this opposite phase air flow modulation together with a base pressure in order to cancel out physiological events such as snoring with a minimum pressure applied to the patient (ie by way of nasal mask). It is desirable to keep the delivery of pressure to the patient at a minimum in order to minimise the discomfort to the patient and also to minimise side effects from therapeutic intervention by way of gas delivery.

The apparatus of the present invention is unique in its ability to produce a servo loop effect in the application of patient gas delivery. By modulating and controlling the base pressure delivery to minimise the sound monitored during snoring episodes (due to the patient's vibrating upper palate), the apparatus may apply a precise amount of opposite phase modulated pressure to stabilize the vibrating the upper palate. The apparatus can provide the combination of base pressure and modulated pressure waveforms by utilising conventional technology to produce a continuous or slowly varying (low frequency) gas delivery—such as a range of pressure (say 0 CMH20 to 20 CMH20 range) with variation of rate of pressure or airflow change from say continuous to 10 cycles per second. At the same time the apparatus may provide a higher frequency modulated gas delivery—such as a range of pressure (say 0 CMH20 to 3 CMH20 range) with variation of rate of pressure or airflow change from say 0.5 cycles per second to say 1000 cycles per second. The apparatus of the present invention may provide these two forms of gas delivery being continuous and higher frequency gas modulation. In one form the latter may be provided by means of a diaphragm (similar to the cone of the driver of an audio loudspeaker) to modulate the low frequency or continuous gas delivery obtainable from a conventional respiratory ventilator or air delivery blower device. One example of the manner in which a continuous gas delivery system may be modified in accordance with the principles of the present invention is described below with reference to FIG. 5.

STEP 6

High frequency pressure rate changes and low frequency base pressure changes may be continuously checked by the system control so as not to exceed pre-programmed patient safety limits. These pressure limits may be detected and checked by way of two methods;

1) System control may limit the amount of base pressure and modulation control output from the system in order to not exceed preset patient limits.
2) The apparatus may monitor gas delivery to the patient by way of a pressure or airflow sensor interfaced to the patient's breathing. This interfaced can be by way of a sensor attached to the patient's breathing mask, for example. The monitored airflow or pressure may be limited by the apparatus to fall within safe patient limits as reprogrammed by the system or the assistant user (supervising medical practitioner).

STEP 7

Step 7 functions to correct any excessive pressure or airflow modulation to remain within safe patient limits.

STEP 8

Step 8 compares microphone signal's current data with the microphone signal's previous data and determines through processes of comparing alignment and subtraction, whether activated pressure changes are having an effect on the amplitude of the respiratory event. That is, is the effect of pressure activation change causing the current respiratory event (ie snoring sound) to reduce in presence as measured by a decrease in the amplitude of the sound signal. Reference may be had to the example waveforms shown in FIGS. 1A to 1F.

STEP 9

Step 9 determines whether pressure or airflow change activation reduce the effect of the respiratory event, ie does snoring subside.

The purpose of this step is to determine whether or not the application of a change of pressure and airflow to the patient is directly related to reducing the symptoms of the patient's respiratory disorder.

STEP 10

Has system "Stop Record" mode or has system pre-programmed stop time been selected or has system power been interrupted or switched off?

STEP 11

Step 11 ends the process and follows step 10 system off selection.

Figure 5:
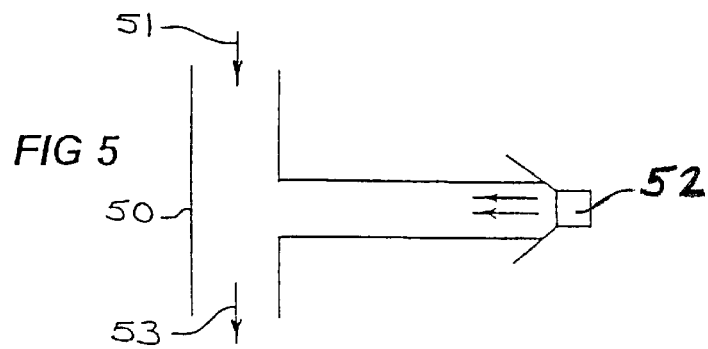
FIG. 5 shows one form of gas delivery system modified in accordance with the principles of the present invention.

FIG. 5 shows one example whereby a continuous gas delivery system can be modified in accordance with the principles of the present invention. Modification is by means of a T section element 50 inserted into the supply of base or continuous pressure or airflow 51 associated with the system. The modification comprises an air pressure modulator 52 (refer module 6 in FIG. 1) placed in communication with the leg of T section element 50 such that air pressure changes produced by modulator 52 are impressed upon the base or continuous pressure or airflow 51 to form a composite pressure/air flow 53. Composite flow 53 comprises a combination of base pressure 51 and modulated pressure/airflow produced via modulator 52. The air pressure changes impressed via modulator 52 are generally of a substantially higher frequency than changes that may be produced by the continuous gas delivery system.

Finally, it is to be understood that various alterations, modifications and/or additions may be introduced into the constructions and arrangements of parts previously described without departing from the spirit or ambit of the invention.

What is claimed is:

1. An apparatus for controlling gas delivery to a patient to maintain effective respiratory function, said apparatus including:
   a monitoring component adapted to monitor at least one physiological variable of a patient during an application of a positive gas pressure to an airway of the patient, to provide monitoring information representing the at least one physiological variable; and
   a processing component including a deriving component in communication with the monitoring component, adapted to receive the monitoring information and, based on the monitoring information, to derive data representing a respiratory event characterized by a vibration of body tissue along the airway;
   said processing component further including a determining component coupled to receive said data and including an algorithm operable to generate a control signal based on said data, said control signal being substantially 180 degrees out of phase relative to said data and being applicable to control a gas delivery device to modulate said positive gas pressure in a manner to counteract said vibration of the body tissue, thereby tending to cancel the respiratory event.

2. The apparatus according to claim 1 wherein said control signal includes a modulated component.

3. The apparatus according to claim 2 wherein said modulated component is substantially 180 degrees out of phase relative to said data representing a respiratory event.

4. The apparatus according to claim 2 wherein said modulated component is adapted to acoustically cancel vibration in an upper palate of the patient.

5. The apparatus according to claim 2 wherein the control signal further includes an additional component selected from the group consisting of: a substantially continuous component, and a component that changes relatively slowly when compared to said modulated component.

6. The apparatus according to claim 1 wherein at least one of said deriving component and said determining component includes a digital processor.

7. The apparatus according to claim 1 wherein the gas delivery device includes a gas pressure valve.

8. The apparatus according to claim 1 wherein the gas delivery device includes an acoustic transducer.

9. The apparatus according to claim 1 further including a device for delivering a drug to the patient.

10. The apparatus according to claim 1 wherein said positive gas pressure, when controlled in accordance with the control signal, is substantially constant.

11. The apparatus according to claim 1 wherein said positive gas pressure, when controlled in accordance with the control signal, is variable.

12. The apparatus according to claim 1 wherein the at least one physiological variable is selected from the group consisting of: breathing airflow, respiratory effort, and breathing sound.

13. The apparatus according to claim 1 wherein the at least one physiological variable is selected from the group consisting of: brain waves, eye movement, heart beat, muscle function, and patient position.

14. The apparatus according to claim 1 wherein the deriving component further is adapted to derive data representing a respiratory state of the patient.

15. The apparatus according to claim 14 wherein the control signal is applicable to control the gas delivery device to control said positive gas pressure in accordance with the control signal to substantially prevent a deterioration in said respiratory state.

16. The apparatus according to claim 14 wherein said deriving component employs an algorithm to derive the data representing a respiratory state.

17. The apparatus according to claim 14 wherein said deriving component is adapted to evaluate at least one state selected from the group consisting of: sleep states, and arousal states.

18. The apparatus according to claim 14 wherein said deriving component is adapted to detect arousals.

19. An apparatus for controlling drug delivery to a patient to maintain effective respiratory function, said apparatus including:
  a monitoring component adapted to monitor at least one physiological variable of a patient during an application of a positive gas pressure to an airway of the patient, to provide monitoring information representing the at least one physiological variable; and
  a processing component including a deriving component in communication with the monitoring component to receive the monitoring information, and, based on the monitoring information, to derive data representing a respiratory state of the patient and further representing a respiratory event characterized by vibration of body tissue along the airway;
  said processing component further including a control component receiving said data and, based on the data, using an algorithm to generate a control signal substantially 180 degrees out of phase relative to said data to control a gas delivery device in a manner to counteract said vibration of the body tissue, thereby tending to cancel the respiratory event, and further adapted to initiate a delivery of a drug to the patient to substantially prevent a deterioration in said respiratory state.

20. The apparatus according to claim 19 wherein said at least one physiological variable is selected from the group consisting of: breathing airflow, and breathing sound.

21. The apparatus according to claim 19 wherein said drug includes ventilum.

22. A method for controlling gas delivery to a patient, said gas delivery being adapted to maintain effective respiratory function, said method including:
  operating a gas delivery device to provide a positive pressure delivery of a gas to an airway of a patient;
  during said delivery, monitoring at least one physiological variable of the patient, to provide monitoring information representing the at least one physiological variable;
  using the monitoring information to derive data representing a respiratory event comprising vibration of body tissue along the airway;
  using the data to generate a control signal, including using an algorithm to generate the control signal, said control signal being substantially 180 degrees out of phase relative to said data;
  using the control signal to modulate said delivery in a manner to counteract said vibration of the body tissue, thereby tending to cancel the respiratory event.

23. The method according to claim 22 wherein said control signal includes a modulated component.

24. The method according to claim 23 wherein said modulated component is substantially 180 degrees out of phase relative to the data representing a respiratory event.

25. The method according to claim 23 filter including using said modulated component to operate a gas delivery device to cancel vibration in an upper palate of the patient.

26. The method according to claim 22 wherein said control signal includes a substantially continuous component.

27. The method according to claim 22 wherein said using the control signal to control delivery of a gas to the patient comprises causing a gas delivery device to provide the gas to the patient at a substantially constant positive pressure.

28. The method according to claim 22 wherein said using the control signal to control delivery of a gas to the patient comprises causing a gas delivery device to provide the gas to the patient at a varying positive pressure.

29. The method according to claim 22 wherein the control signal further includes an additional component selected from the group consisting of: a substantially continuous component, and a component that changes relatively slowly when compared to said modulated component.

30. The method according to claim 22 wherein monitoring the at least one physiological variable includes monitoring a physiological variable selected from the group consisting of: breathing air flow, respiratory efforts and breathing sound.

31. The method according to claim 22 wherein monitoring the at least one physiological variable includes monitoring physiological variable selected from the group consisting of: brain waves, eye movement, heart beat, muscle function, and patient position.

32. The method according to claim 22 further including using the monitoring information to derive data representing a respiratory state of the patient corresponding to the at least one physiological variable.

33. The method according to claim 32 wherein said using the control signal to control delivery of a gas to the patient comprises causing a gas delivery device to substantially prevent a deterioration in said respiratory state.

34. An apparatus for controlling gas delivery to a patient to maintain effective respiratory function, said apparatus including:
- a monitoring component adapted to monitor at least one physiological variable of a patient during an application of a positive gas pressure to an airway of the patient, to provide monitoring information representing the at least one physiological variable; and
- a processing component including a deriving component in communication with the monitoring component to receive the monitoring information, and, based on the monitoring information, to derive data representing a respiratory event characterized by vibration of body tissue along the airway;
- said processing component further including a determining component coupled to receive said data and adapted to generate a control signal based on said data, said control signal including a modulated component substantially 180 degrees out of phase relative to said data representing a respiratory event and being applicable to control a gas delivery device to modulate said positive gas pressure in accordance with the modulated component of the control signal to counteract said vibration of body tissue, thereby tending to cancel the respiratory event.

35. The apparatus according to claim 34 wherein said modulated component is adapted to acoustically cancel vibration in an upper palate of the patient.

36. The apparatus according to claim 34 wherein said control signal further includes an additional component selected from the group consisting of: a substantially continuous component, and a component that changes relatively slowly when compared to said modulated component.

37. A method for controlling gas delivery to a patient, said gas delivery being adapted to maintain effective respiratory function, said method including:
- operating a gas delivery device to provide a positive pressure delivery of a gas to an airway of a patient;
- during the delivery, monitoring at least one physiological variable of a patient, to provide monitoring information representing the at least one physiological variable;
- using the monitoring information to derive data representing a respiratory event including vibration of body tissue along the airway;
- using the data to generate a control signal that includes a modulated component that is substantially 180 degrees out of phase relative to the data representing the respiratory event; and
- using the modulated component of the control signal to modulate the positive pressure of the gas to counteract said vibration of the body tissue, thereby tending to cancel the respiratory event.

38. The method according to claim 37 further including using said modulated component to operate a gas delivery device to cancel vibration in an upper palate of the patient.

* * * * *